United States Patent [19]

Malen et al.

[11] Patent Number: 5,030,646
[45] Date of Patent: Jul. 9, 1991

[54] NOVEL TRICYCLIC INDOLE COMPOUND

[75] Inventors: Charles Malen, Fresnes; Jean-Michel Lacoste, Sevres; Michel Laubie, Vaucresson, all of France

[73] Assignee: Adir et Compagnie, Neuilly-sur-Seine, France

[21] Appl. No.: 446,034

[22] Filed: Dec. 5, 1989

[30] Foreign Application Priority Data

Dec. 6, 1988 [FR] France ............... 88 15937

[51] Int. Cl.$^5$ ............... A61K 31/415; C07D 413/00; C07D 279/10; C07D 491/00
[52] U.S. Cl. .................... 514/397; 548/430; 548/432; 548/336; 548/327; 514/411; 514/321; 514/232.8; 514/394; 514/395; 514/228.2; 546/198; 544/142; 544/58.7
[58] Field of Search ............... 548/430, 432, 336, 327; 514/411, 275, 218, 397, 321, 232.8, 394, 395, 228.2; 544/335, 142, 58.7; 540/492; 546/198

[56] References Cited

U.S. PATENT DOCUMENTS 4,092,328 5/1978 Brown .................. 548/430

Primary Examiner—Mary C. Lee
Assistant Examiner—Robert C. Whittenbaugh
Attorney, Agent, or Firm—Gordon W. Hueschen

[57] ABSTRACT

The invention relates to compounds of general formula:

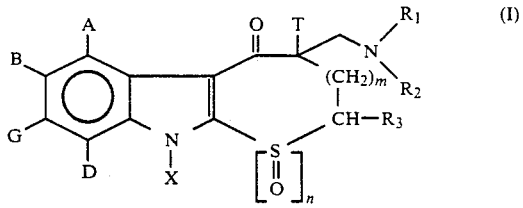

in which
A, B, G, D which may be identical or different, each denote a hydrogen atom or a halogen atom, a lower alkoxy group or alternatively a lower alkyl group optionally substituted with one or more halogen atoms, X denotes a hydrogen atom, a linear or branched lower alkyl group or a group $SO_2E$ in which E denotes a linear or branched lower alkyl group or an aryl group optionally substituted with a linear or branched lower alkyl group, T denotes a hydrogen atom or a lower alkyl group, $R_3$ denotes a hydrogen atom or a linear or branched lower alkyl group or an aryl group optionally substituted with one or more linear or branched lower alkyl groups, n and m, which may be identical or different, each denote 0 or 1, $R_1$ and $R_2$, which may be identical or different, each denote a hydrogen atom or a linear or branched lower alkyl group, or alternatively, $R^1$ and $R^2$ form, together with the nitrogen atom to which they are linked, a saturated or unsaturated, mono- or bicyclic nitrogenous heterocyclic system, each ring being 5- or 6-membered and optionally comprising one or two other hetero atoms selected from nitrogen, oxygen or sulfur, and optionally substituted with one or more linear or branched lower alkyl or alkoxy groups or with an aryl group which is itself optionally substituted with one or more lower alkyl, lower alkoxy or trifluoromethyl groups or alternatively one or more halogen atoms, or alternatively, $R^1$ denotes a group

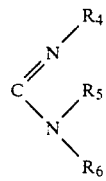

in which $R_4$, $R_5$ and $R_6$, which may be identical or different, each denote a hydrogen atom or a linear or branched lower alkyl group, or alternatively $R_4$ forms with $R_5$ a bridge $(CH_2)_p$, p being between 2 and 4, or alternatively $R_1$ denotes a dibenzo[a,d]cyclohept-5-yl group and $R_2$ denotes a hydrogen atom, where appropriate, their isomers and also their addition salts with a pharmaceutically acceptable acid. Medicinal products.

8 Claims, No Drawings

NOVEL TRICYCLIC INDOLE COMPOUND

The present invention relates to new indole compounds, to a process for preparing them and to pharmaceutical compositions containing them.

More especially, the invention relates to compounds possessing antagonist properties with respect to 5-hydroxytryptamine (5-HT) receptors, more especially to 5-HT$_3$ receptors, which receptors are known to be implicated in many disorders of both a central and a peripheral nature.

The antagonist properties with respect to 5-HT$_3$ receptors of a number of tetrahydro-4-carbazolones, described, in particular, in European Patent Applications Nos. 0,191,562, 0,210,840, 0, 219, 929, 0,275,668 and 0,275,669 and also in French Patent Application 2,601,951, are already known. Among all the compounds described in these patent applications, one, designated GR 38032, possesses potent antagonist activity with respect to 5-HT$_3$ receptors. The compound in question is the compound of formula:

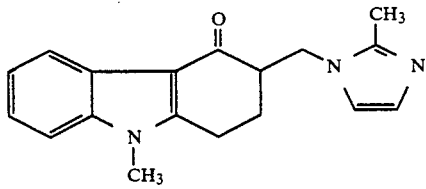

The Applicant has now discovered new indole compounds whose antagonist activity with respect to 5-HT$_3$ receptors is significantly greater than that of the reference compound GR 38032. In addition, their duration of action is sufficiently longer, thereby rendering them better suited to therapeutic application.

More specifically, the present invention relates to compounds of formula (I):

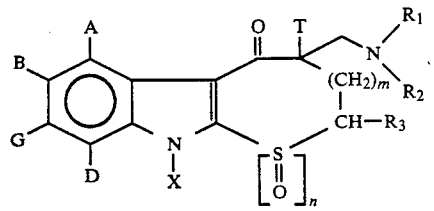

in which:
- A, B, G and D, which may be identical or different, each denote a hydrogen atom or a halogen atom, a lower alkoxy group or alternatively a linear or branched lower alkyl group optionally substituted with one or more halogen atoms,
- X denotes a hydrogen atom, a linear or branched lower alkyl group or a group SO$_2$E in which E denotes a linear or branched lower alkyl group or an aryl group optionally substituted with a linear or branched lower alkyl group,
- T denotes a hydrogen atom or a lower alkyl group,
- R$_3$ denotes a hydrogen atom or a linear or branched lower alkyl group or an aryl group optionally substituted with one or more linear or branched lower alkyl groups,
- n and m, which may be identical or different, each denote 0 or 1,
- R$_1$ and R$_2$, which may be identical or different, each denote a hydrogen atom or a linear or branched lower alkyl group, or alternatively, R$^1$ and R$^2$ form, together with the nitrogen atom to which they are linked, a saturated or unsaturated, mono- or bicyclic nitrogenous heterocyclic system, each ring being 5-or 6-membered, optionally comprising one or two other hetero atoms selected from nitrogen, oxygen or sulfur, optionally substituted with one or more linear or branched lower alkyl or alkoxy groups or with an aryl group which is itself optionally substituted with one or more lower alkyl, lower alkoxy or trifluoromethyl groups or alternatively one or more halogen atoms, or alternatively, R$^1$ denotes a group

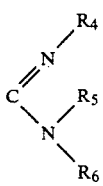

in which R$_4$, R$_5$ and R$_6$, which may be identical or different, each denote a hydrogen atom or a linear or branched lower alkyl group, or alternatively R$_4$ forms with R$_5$ a bridge (CH$_2$)$_p$, p being between 2 and 4, or alternatively R$_1$ denotes a 10,11-dihydro-5H-dibenzo[a,d]cyclohepten-5-yl group and R$_2$ denotes a hydrogen atom, where appropriate, their isomers and also their addition salts with a pharmaceutically acceptable acid, on the understanding that lower alkyl or lower alkoxy group means groups comprising from 1 to 6 carbon atoms.

Among acids which may be added to the compounds of formula (I) to form an addition salt, hydrochloric, sulfuric, phosphonic, tartaric, malic, maleic, fumaric, oxalic, succinic, methanesulfonic, ethanesulfonic, camphoric and citric and the like, may be mentioned by way of example.

The invention also encompasses the process for obtaining the compounds of the formula (I), wherein a compounds of formula (II):

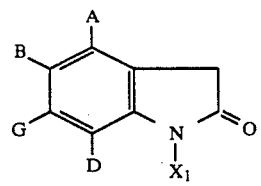

in which A, B, G and D have the same meaning as in the formula (I), and X$_1$ denotes a hydrogen atom or a lower alkyl group, is condensed and treated in the presence of a thionating agent such as phosphorus pentasulfide to obtain a compound of formula (III):

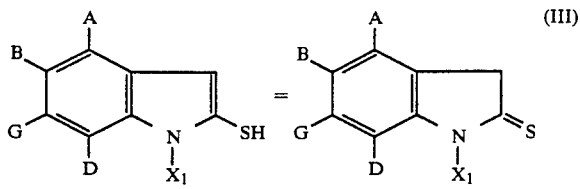

in which A, B, G, D and $X_1$ have the same meaning as above, which is treated with a compound of formula (IV):

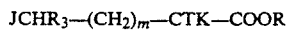

JCHR$_3$—(CH$_2$)$_m$—CTK—COOR     (IV)

in which:
either m denotes 0, and in this case J and K together denote a $\pi$ bond,
or m denotes 1 and in this case J denotes a halogen atom and K denotes a hydrogen atom, and
R denotes a hydrogen atom or a linear or branched lower alkyl group and T and R$_3$ have the same meaning as in the formula (I),
to obtain a compound of the formula (V):

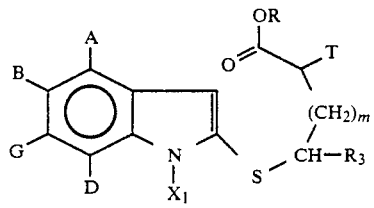

in which A, B, G, D, T, R, R$_3$, $X_1$ and m have the same meaning as above, which, when R is other than H, is subjected to the action of an alkaline agent to lead to a derivative of formula (Va), a special case of the compounds of formula (V) for which R denotes H,

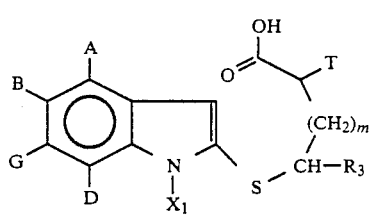

which is subjected to the action of polyphosphate ester prepared according to W. POLLMAN and G. SCHRAMM (Biochem Biophysica Acta, 1963, 80, 1), preferably under a nitrogen atmosphere, to lead to a compound of formula (VI):

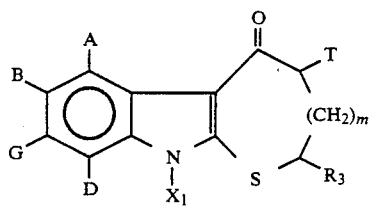

in which A, B, G, D, T, m, $X_1$ and R$_3$ have the same meaning as above, which is then treated with paraformaldehyde, preferably under a nitrogen atmosphere, in the presence of a dialkylamine

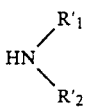

or a salt thereof with a strong acid, in which R$'_1$ and R$'_2$ denote lower alkyl, to lead to a compound of formula (I/A), a special case of the compounds of formula (I):

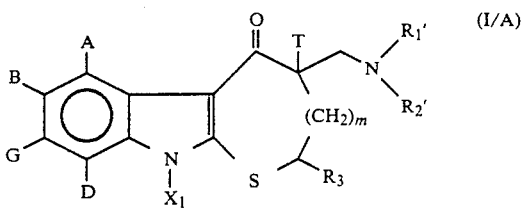

in which A, B, G, D, R$_3$, T, m and $X_1$ have the same meaning as above and R$'_1$ and R$'_2$ denote a lower alkyl group, which is purified, if necessary, by chromatography and/or crystallization and which, when, in the compound of formula (I) which it is desired to obtain, R$_1$ and R$_2$ form, with the nitrogen atom to which they are attached, a heterocyclic system as defined in the formula (I), is then treated with a nitrogenous heterocyclic compound, the nitrogen atom being linked to a hydrogen atom, the heterocyclic compound being mono- or bicyclic and saturated or unsaturated, each ring being 5- or 6-membered and optionally comprising one or two other hetero atoms selected from nitrogen, oxygen or sulfur, and optionally substituted with one or more linear or branched lower alkyl or alkoxy groups or with an aryl group which is itself optionally substituted with one or more lower alkyl, lower alkoxy or trifluoromethyl groups or alternatively one or more halogen atoms, to give a compound of formula (I/B):

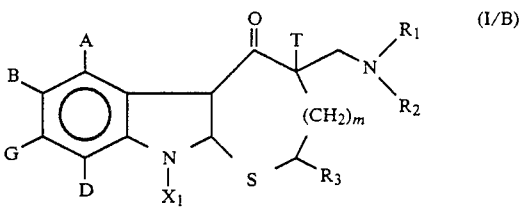

a special case of the compounds of formula (I) in which A, B, G, D, R$_3$, T, m and $X_1$ have the same meaning as above and R$_1$ and R$_2$ form, with the nitrogen atom to which they are attached, a heterocyclic system as defined above, and when, in the compound of formula (I) which it is desired to obtain, R$_1$ and R$_2$ each denote a hydrogen atom, is treated with 10, 11, dihydro-5H-dibenzo[a,d]cyclohepten-5-ylamine to lead, after purification by chromatography and crystallization, to a compound of formula (I/C1):

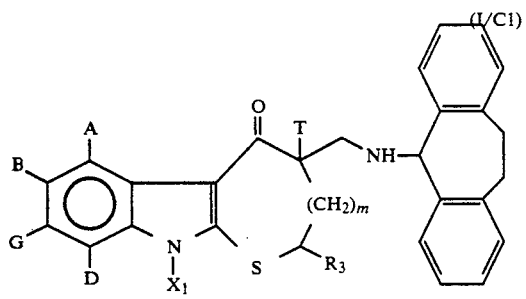

a special case of the formula (I) in which A, B, G, D, R₃, T, m and X₁ have the same meaning as above, which is treated by heating in acetic acid, where appropriate dilute, to lead, after optional crystallization, to a compound of formula (I/C):

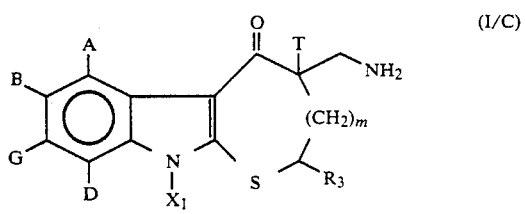

a special case of the compounds of formula (I) in which A, B, G, D, R₃, T, m and X₁ have the same meaning as above, which is purified, if necessary, by chromatography and/or crystallization and which, when, in the compound of formula (I) which it is desired to obtain, R₁ denotes a group:

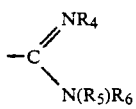

in which R₄, R₅ and R₆ have the same definition as in the formula (I), is treated with a salt with a strong acid of a compound of formula (VII):

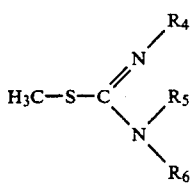

in which R₄, R₅ and R₆ have the same definition as in the formula (I), to lead, after optional purification by chromatography, treatment with a heavy metal salt and optional crystallization, to a compound of formula (I/D):

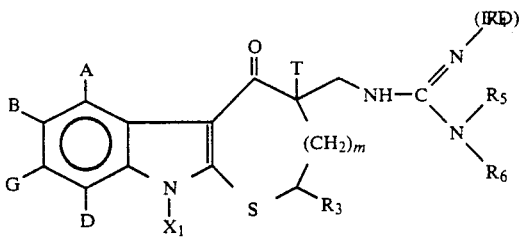

a special case of a compound of formula (I) in which R₁ denotes a group:

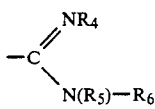

and R₂ denotes a hydrogen atom, and where A, B, G, D, R₃, T, m and X₁ have the same meaning as above, which, in the case where X₁ denotes a hydrogen atom, may be subjected, depending on the compound of formula (I) which it is desired to obtain, to the action of a compound of formula (VIII):

Hal—SO₂E   (VIII)

in which E has the same meaning as in the formula (I) and Hal denotes a halogen atom, in the presence of sodium hydride, to lead, after extraction and optional purification by column chromatography, to a compound of formula (I/E):

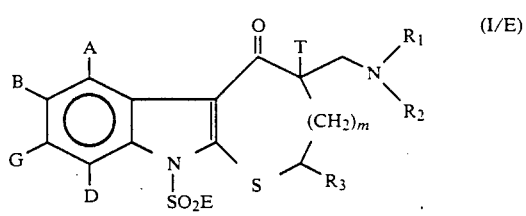

a special case of the compounds of formula (I) in which X denotes SO₂E and where A, B, G, D, R₁, R₂, R₃, T, m and E have the same meanings as in the formula (I), which compounds of formula (I/A), (I/B), (I/C1), (I/C), (I/D) or (I/E), in the case where n denotes 1 in the compound of formula (I) which it is desired to obtain, is treated with an oxidizing agent, preferably meta-chloro-perbenzoic acid, to lead, after optional purification by chromatography and/or crystallization, to the compound of formula (I/F):

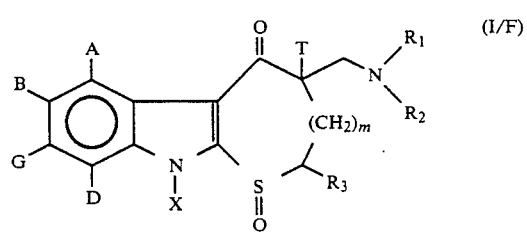

a special case of the compounds of formula (I) in which A, B, G, D, X, T, R₁, R₂, R₃ and m have the same meaning as in the formula (I), n here denoting 1, which compound of formula (I/A), (I/B), (I/C1), (I/C), (I/D), (I/E) or (I/F), if so desired, may, if appropriate, be separated into its isomers, and/or either salified to facilitate its purification for possible subsequent stages, or salified with a pharmaceutically acceptable acid and optionally crystallized for use for therapeutic purposes.

The compounds of formula (I) and also their addition salts with a pharmaceutically acceptable acid possess advantageous pharmacological properties.

In particular, the compounds of the present invention show especially intense and surprisingly longlasting antagonist activity with respect to 5-HT$_3$ serotonin receptors.

In particular, the compounds of the present invention, administered intravenously to rats at doses of between 10 µg/kg and 1 mg/kg, antagonize the Bezold-Jarish effect (bradycardia and hypotension after injection of serotonin) intensively and for an extended period of time. This property is indicative of an antagonist effect on 5-HT$_3$ receptors.

Accordingly, the compounds of the present invention find their therapeutic applications in the treatment of conditions stemming from a dysfunction of the serotoninergic system, and in which blocking of the 5-HT$_3$ receptors—either central or peripheral—is said to be capable of having beneficial effects.

Among these conditions, there may be mentioned migraine and, more generally, painful episodes, anxiety, schizophrenia, vomiting and, in particular, that following the administration of anticancer treatments, heart rhythm disorders, some gastrointestinal upsets and also cognitive disorders and especially dementia states and memory disorders.

The subject of the invention is also pharmaceutical compositions containing a compound of formula (I) or one of its addition salts with a pharmaceutically acceptable acid, alone or in combination with one or more pharmaceutically acceptable, non-toxic, inert vehicles or excipients.

Among the pharmaceutical compositions according to the invention, there may be mentioned, more especially, those which are suitable for parenteral, peror transcutaneous, nasal, rectal, perlingual, ocular or respiratory administration, and in particular injectable preparations, aerosols, eye or nose drops, capsules, hard gelatin capsules, tablets, sublingual tablets, sublingual preparations, bars, suppositiories, creams, ointments, skin gels and the like.

The appropriate dosage will vary according to the patient's age and weight, the administration route and the nature of the therapeutic indication and of any associated treatments, and will range between one microgram and one gram per dose or per application.

Examples which follow illustrate the invention and in no way limit the latter.

The melting points stated are measured according to the micro-Kofler technique. The $^1$H nuclear magnetic resonance spectra were recorded using TMS as internal reference.

EXAMPLE 1

3-[(2-Methyl-1-Imidazolyl)Methyl]-4-Oxo-9-Methyl-2,3,4,6-Tetrahydrothiopyrano[2,3-b]Indole (Hydrochloride)

Stage A: 1-Methyl-2-Indolinethione 148 g (1.76 mol) of sodium bicarbonate are added in 20-gram portions with brisk stirring and at room temperature to a suspension of 130 g (0.8 mol) of 1-methyl-2-indolinone, prepared according to R. A. ABRAMOVITCH and D. H. HEY (J. Chem. Soc., 1954, 1699) and 133 g (0.3 mol) of phosphorus pentasulfide in 1.30 l of anhydrous tetrahydrofuran. After 10 hours' stirring at room temperature, the mixture is filtered and the filtrate is concentrated on a water bath under vacuum. The residue is taken up with a water/ice mixture and the resulting mixture is extracted three times with chloroform. The organic phase is washed with water and then with saturated aqueous sodium chloride solution, dried and evaporated to dryness. The residue is recrystallized in methanol.

Yield: 93%.

Melting point: 177°–118° C.

Analysis: Calculated: C: 66.22, N: 8.58, S: 19.64. Found: C: 66.62, N: 8.63, S: 19.76.

Stage B: 3-(1-Methyl-2-Indolylthio)Propionic Acid 600 ml of triethylamine are added slowly to a vigorously stirred suspension of 100 g (0.613 mol) of 1-methyl-2-indolinethione, obtained in stage A, in 46.8 g (0.65 mol) of acrylic acid. The mixture is heated to reflux for 12 hours, allowed to cool and concentrated under vacuum. The residue is taken up with 10% strength aqueous sodium bicarbonate solution and filtered. The filtrate is treated with twofold diluted hydrochloric acid until a pH in the region of 3 is obtained. The precipitate is drained, washed with water and dried. The product is recrystallized in toluene.

Yield: 70%.

Melting point: 117°–119° C.

Analysis: Calculated: C: 61.25, H: 5.57, N: 5.95, S: 13.63. Found: C: 61.66, H: 5.64, N: 5.72, S: 13.71.

Stage C:
4-Oxo-9-Methyl-2,3,4,9-Tetrahydrothiopyrano[2,3-b]Indole 88.2 G (0.375 mol) of 3-(1-methyl-2-indolylthio)propionic acid obtained in stage B, and 300 g of polyphosphate ester, prepared according to W. POLLMANN and G. SCHRAMM (Biochem. Biophysica Acta, 80, 1 (1963)), are placed in 3.5 l of chloroform. The mixture is stirred at room temperature and under a nitrogen atmosphere for 16 hours. After hydrolysis with 3 liters of ice-cold water, the organic phase is separated after settling has occurred and the aqueous phase is extracted twice with chloroform. The organic phases are combined, washed with 10% strength sodium bicarbonate solution and then with water and dried, and the organic medium is evaporated off on a water bath under vacuum. The residue is recrystallized in acetonitrile.

Yield: 87%.

Melting point: 164°–165° C.

Analysis: Calculated: C: 66.33, H: 5.10, N: 6.45, S: 14.76. Found C: 66.18, H: 5.02, N: 6.55, S: 14.72.

Stage D:
3-[(Dimethylamino)Methyl]-4-Oxo-9-Methyl-2,3,4,9-Tetrahydrothiopyrano-[2,3-]Indole 21.7 g (0.1 mol) of 4-oxo-9-methyl-2,3,4,9-tetrahydrothiopyrano[2,3-b]indole, 16.3 g (0.2 mol) of dimethylamine hydrochloride and 6 g of paraformaldehyde are suspended in 280 ml of acetic acid. The mixture is heated to 100° C. with brisk stirring and under a nitrogen atmosphere for 2 hours. After the mixture is cooled, the solvent is evaporated off and the residue is taken up with an acetic acid/water mixture (20:80). The resulting mixture is washed with ethyl acetate and alkalinized with concentrated ammonia solution. The precipitate obtained is drained, washed with water, dried and recrystallized in ethanol.

Yield: 65%.
Melting point: 110°–112° C.

Stage E:
3-[(Dimethylamino)Methyl]-4-Oxo-9-Methyl-2,3,4,9-Tetrahydrothiopyrano[2,3-b]Indole (Hydrochloride)

The 3-[(dimethylamino)methyl]-4-oxo-9-methyl-2,3,4,9-tetrahydrothiopyrano[2,3-b]indole obtained in stage D is dissolved in 200 ml of tetrahydrofuran. The solution is treated with an ethereal solution of hydrochloric acid overnight. The product formed is drained, washed with ethyl ether, dried and recrystallized in ethanol.

Yield: 80%.
Melting point: 280°–283° C.
Analysis: Calculated: C: 57.95, H: 6.16, N: 9.01, S: 10.31. Found: C: 57.53, H: 6.48, N: 8.94, S: 10.31.

Stage F:
3-[(2-Methyl-1-Imidazolyl)Methyl]-4-Oxo-9-Methyl-2,3,4,9-Tetrahydrothiopyrano[2,3-b]Indole (Hydrochloride)

A solution of 1.3 g (0.0158 mol) of 2-methylimidazole and 1.80 g (0.0057 mol) of 3-[(dimethylamino)methyl]-4-oxo-9-methyl-2,3,4,9-tetrahydrothiopyrano[2,3-b]indole hydrochloride, obtained in the preceding stage, in 25 ml of water is heated to reflux for 20 hours. After the mixture is cooled, the product is drained and the residue obtained is washed with water and dried. The solid is dissolved in hot ethanol and treated with ethanolic hydrochloric acid solution. The mixture is evaporated and the product is crystallized in ethanol.

Yield: 75%.
Melting point: 232°–234° C.
Analysis: Calculated: C: 58.70, H: 5.22, N: 12.08. S: 9.22, Cl: 10.19. Found: C: 58.51, H: 5.29, N: 12.07. S: 9.30, Cl: 10.33.

Spectral characteristics: $^1$H NMR Solvent $D_2O$ $\delta$ (ppm) $\delta = 2.40$, singlet, 3H, =N—C(CH$_3$)=N, $\delta = 2.60$–3.40 ppm, complex, 3H, S—CH$_2$ and CO—CH, $\delta = 3.20$ ppm, singlet, 3H, =N—CH$_3$, $\delta = 4.10$–4.40 ppm, multiplet, 2H—CH$_2$—N, $\delta = 7.10$–7.80 ppm, complex, 6H, aromatic and ethylenic

EXAMPLE 2:

2,9-Dimethyl-3-[(2-Methyl-1-Imidazolyl)Methyl]-4-Oxo-2,3,4,9-Tetrahydrothipyrano[2,3-b]Indole (Hydrochloride)

Stage A: 3-(1-Methyl-2-Indolylthio)-3-Methyl Propionic Acid

A mixture of 16.30 g (0.01 mol) of 1-methyl-indoline-2-thione, obtained in Example 1, stage A, 8.61 g (0.01 mol) of crotonic acid and 5 drops of piperidine is brought to approximately 140° C. with stirring for 6 hours. The mixture is allowed to cool and is taken up with 500 ml of 5% strength sodium hydroxide and the aqueous phase is washed with ethyl acetate, acidified with hydrochloric acid and extracted 3 times with methylene chloride. The organic phases are dried and concentrated on a water bath under vacuum. The residue is used in the next stage without further treatment.

Yield: 70%.

Stage B:
2,9-Dimethyl-4-Oxo-2,3,4,9-Tetrahydrothiopyrano[2,3-b]Indole

A mixture of 16.20 g (0.065 mol) of 3-(1-methyl-2-indolylthio)-3-methylpropanoic acid, obtained in the preceding stage, and 70 g of polyphosphate ester in 500 ml of chloroform is stirred at room temperature under a nitrogen atmosphere for 3 hours. The mixture is diluted with 800 ml of ice-cold water, the organic phase is separated after settling has occurred and the aqueous phase is extracted three times with chloroform. The organic phases are combined and washed with 10% strength aqueous bicarbonate solution and then with water and dried, and the solvent is evaporated off. The residue is recrystallized in acetonitrile.

Yield: 60%.
Melting point: 159°–160° C.
Analysis: Calculated: C: 67.50, H: 5.66, N: 6.06, S: 13.86. Found: C: 67.44, H: 5.74, N: 6.14, S: 13.85.

Stage C: 2,9-Dimethyl-3-[(Dimethylamino)Methyl]4-Oxo-2,3,4,9-Tetrahydrothiopyrano[2,3-b]Indole (Hydrochloride)

A suspension of 6 g (0.026 mol) of 2,9-dimethyl-4-oxo-2,3,4,9-tetrahydrothiopyrano[2,3-b]indole, obtained in the preceding stage, 4.29 g (0.052 mol) of dimethylamine hydrochloride and 0.40 g of paraformaldehyde in 100 ml of acetic acid is stirred at 100° C. under a nitrogen atmosphere for 2 h 30 min. The mixture is cooled, the solvent is evaporated off and the residue is taken up with 250 ml of water. The aqueous phase is washed with ethyl acetate, alkalinized with concentrated ammonia solution and extracted three times with methylene chloride. The organic phases are combined, washed with saturated sodium chloride solution and dried, and the solvent is evaporated off. The residue is dissolved in 50 ml of tetrahydrofuran and the solution is treated with an ethereal solution of hydrochloric acid. The precipitate formed is drained, washed with ether and recrystallized in ethanol.

Yield: 60%.
Melting point: 242°–244° C.
Analysis: Calculated: C: 59.15, H: 6.52, N: 8.62, S: 9.87, Cl: 10.91. Found: C: 58.82, H: 6.83, N: 8.46, S: 9.83, Cl: 10.78.

Stage D:
2,9-Dimethyl-3-[(2-Methyl-1-Imidazolyl)Methyl]-4-Oxo-2,3,4,9-Tetrahydrothiopyrano[2,3-b]Indole (Hydrochloride)

A solution of 2 g (0.062 mol) of 2,9-dimethyl-3-[(dimethylamino)methyl]-4-oxo-2,3,4,9-tetrahydrothiopyrano[2,3-b]indole hydrochloride and 1.64 g (0.020 mol) of 2-methylimidazole in 30 ml of water is stirred under reflux under a nitrogen atmosphere for 16 hours. After the mixture is cooled, the precipitate formed is drained, washed with water and dried. The powder obtained is dissolved in 30 ml of tetrahydrofuran and the solution is treated with an ethereal solution of hydrochloric acid. The precipitate formed is drained, washed with ether, dried and recrystallized in ethanol. The two cis-trans isomers are obtained in a 50:50 ratio.

Yield: 75%.
Melting point: 205°–207° C.
Analysis: Calculated: C: 59.74, H: 5.57, N: 11.61, S: 8.86, Cl: 9.80. Found: C: 59.66, H: 5.54, N: 11.23, S: 8.63, Cl: 9.94.

EXAMPLE 3

3-[(2-Methyl-1-Imidazolyl)Methyl]-4-Oxo-6-Methoxy-9-Methyl-2,3,4,9-Tetrahydrothiopyrano[2,3-b]Indole (Hydrochloride)

Stage A: 1-Methyl-5-Methoxy-2-Indolinethione 18.5 g (0.22 mol) of sodium bicarbonate are added to a solution of 19.5 g (0.11 mol) of 5-methoxy-1-methyl-2-indolinone prepared according to A. H. BECKETT, R. W. DAISLEY and J. WALKER (Tetrahedron 1968, 24 6093) and 16.5 g (0.037 mol) of phosphorus pentasulfide in 200 ml of tetrahydrofuran. The reaction medium is heated to a temperature of 50° C. for 1 h 30 min and then filtered and concentrated on a water bath under vacuum. The residue is taken up with ice-cold water and the mixture is extracted with methylene chloride. The organic phase is washed with saturated sodium chloride solution, dried and evaporated. The residue is used in the next stage without further treatment.

Yield: 94%.

Melting point: 142°–144° C.

Analysis: Calculated: C: 62.15, H: 5.74, N: 7.25, S: 16.59. Found: C: 62.18, H: 5.74, N: 7.06, S: 16.64.

Stage B:
3-(1-Methyl-5-Methoxy-2-Indolylthio)Propanoic Acid 90 ml of triethylamine are added dropwise to a vigorously stirred suspension of 19.5 g (0.1 mol) of 5-methoxy-1-methyl-2-indolinethione obtained in the preceding stage, in 7.55 ml (0.11 mol) of acrylic acid. The reaction medium is heated to reflux for 6 hours and then cooled and concentrated under vacuum. The residue is taken up with 10% strength aqueous bicarbonate solution, the mixture is filtered and the solution obtained is acidified with hydrochloric acid. After the precipitate formed is drained, washed with water and dried, it is recrystallized in toluene.

Yield: 91%.

Melting point: 136°–138° C.

Analysis: Calculated: C: 58.85, H: 5.70, N: 5.28, S: 12.08. Found: C: 58.57, H: 5.80, N: 5.29, S: 11.89.

Stage C:
4-Oxo-6-Methoxy-9-Methyl-2,3,4,9-Tetrahydrothiopyrano[2,3-b]Indole

A mixture of 24 g (0.09 mol) of 3-(1-methyl-5-methoxy-2-indolythio)propanoic acid, obtained in the preceding stage, and 120 g of polyphosphate ester in 80 ml of chloroform is stirred for 16 hours under a nitrogen atmosphere and at room temperature. The reaction mixture is poured into 1 liter of ice-cold water, the organic phase is separated after settling has occurred and the aqueous phase is extracted three times with chloroform. The organic phases are combined, washed with 10% strength aqueous bicarbonate solution and then with water, dried and evaporated. The residue is recrystallized in ethyl acetate.

Yield: 60%.

Melting point: 165°–166° C.

Analysis: Calculated: C: 63.14, H: 5.30, N: 5.66, S: 12.96. Found: C: 62.75, H: 5.48, N: 5.82, S: 12.87.

Stage D:
3-[(Dimethylamino)Methyl]-4-Oxo-6-Methoxy-9-Methyl-2,3,4,9-Tetrahydrothiopyrano](2,3-b)Indole (Hydrochloride)

A suspension of 5.80 g (0.0235 mol) of 4-oxo-6-methoxy-9-methyl-2,3,4,9-tetrahydrothiopyrano[2,3-b]indole, obtained in the preceding stage, 3.83 g (0.047 mol) of dimethylamine hydrochloride and 1.30 g of paraformaldehyde in 70 ml of acetic acid is heated to 100° C. for 1 hour under a nitrogen atmosphere and with vigorous stirring. After the mixture is cooled, the solvent is evaporated and the residue is dissolved in 250 ml of water. The aqueous phase is washed twice with 50 ml of ethyl acetate and alkalinized with concentrated ammonia solution. The precipitate is drained, washed with water, dried and dissolved in 60 ml of tetrahydrofuran. The solution is treated with an ethereal solution of hydrochloric acid. The precipitate formed is drained, washed with ethyl ether, dried and recrystallized in ethanol.

Yield: 35%.

Melting point: 190°–192° C.

Analysis: Calculated: C: 56.38, H: 6.21, N: 8.22, S: 9.41, Cl: 10.40. Found: C: 56.62, H: 5.98, N: 8.12, S: 9.65, Cl: 10.48.

Stage E:
3-[(2-Methyl-1-Imidazolyl)Methyl]-4-Oxo-6-Methoxy-9-Methyl-2,3,4,9-Tetrahydrothiopyrano[2,3,-b]Indole (Hydrochloride)

A solution of 2.10 g (0.0062 mol) of 3-[(dimethylamino)methyl]-4-oxo-6-methoxy-9-methyl-2,3,4,9-tetrahydrothiopyrano[2,3-b]indole hydrochloride and 1.53 g (0.0186 mol) of 2-methylimidazole in 30 ml of water is heated to reflux for 16 hours under a nitrogen atmosphere. After the mixture is cooled, the precipitate is drained, washed with water and dried. The powder obtained is dissolved in 20 ml of ethyl acetate and the solution is treated with an ethanolic solution of hydrochloric acid. After evaporation, the product is recrystallized in ethanol.

Yield: 40%.

Melting point: 196°–197° C.

Analysis: Calculated: C: 57.21, H: 5.33, N: 11.12, S: 8.48, Cl: 9.38. Found: C: 56.42, H: 5.11, N: 10.72, S: 8.47, Cl: 9.28.

EXAMPLE 4

3-[(2-Methyl-1-Imidazolyl)Methyl]-4-Oxo-5-Methoxy-9-Methyl-2,3,4,9-Tetrahydrothiopyrano[2,3-b]Indole (Maleate)

Stage A: 1-Methyl-4-Methoxy-2-Indolinethione

Using the procedure described in Example 3, but replacing 5-methoxy-1-methyl-2-indolinone by 4-methoxy-1-methyl-2-indolinone, the expected product is obtained.

Yield: 80%.

Melting point: 144°–145° C.

Analysis: Calculated: C: 62.15, H: 5.74, N: 7.25, S: 16.59. Found: C: 61.79, H: 5.59, N: 7.10, S: 16.75.

STAGE B: 3-(1-Methyl-4-Methoxy-2-Indolylthio) Propanoic Acid

Using the procedure described in Example 3, stage B, but replacing 1-methyl-5-methoxy-2-indolinethione by 1-methyl-4-methoxy-2-indolinethione obtained in the preceding stage, the expected product is obtained.

Yield: 84%.

Melting point: 126°–128° C.

Analysis: Calculated: C: 58.85, H: 5.70, N: 5.28, S: 12.08. Found: C: 58.70, H: 5.47, N: 5.28, S: 12.03.

STAGE C:
4-Oxo-5-Methoxy-9-Methyl-2,3,4,9-Tetrahydrothiopyrano[2,3-b]Indole

Using the procedure described in Example 3, stage C, but replacing 3-(1-methyl-5-methoxy-2-indolylthio)-propanoic acid by 3-(1-methyl-4-methoxy-2-indolylthio)-propanoic acid obtained in the preceding stage, the expected product is obtained.
Yield: 84%.
Melting point: 162°–163° C.
Analysis: Calculated: C: 63.14, H: 5.30, N: 5.66, S: 12.96. Found: C: 63.02, H: 5.40, N: 5.61, S: 12.61.

STAGE D:
3-[(Dimethylamino)Methyl]-4-Oxo-5-Methoxy-9-Methyl-2,3,4,9-Tetrahydrothiopyrano[2,3-b]Indole (Hydrochloride)

Using the procedure described in Example 3, stage D, but replacing 4-oxo-6-methoxy-9-methyl-2,3,4,9-tetrahydrothiopyrano[2,3-b]indole by 4-oxo-5-methoxy-9-methyl-2,3,4,9-tetrahydrothiopyrano[2,3-b]indole, the expected product is obtained.
Yield: 44%.
Melting point: 200°–202° C.

STAGE E:
3-[(2-Methyl-1H-Imidazol-1-Yl)Methyl]-4-Oxo-5-Methoxy-9-Methyl-2,3,4,9-Tetrahydrothiopyrano[2,3-b]Indole (Maleate)

Using the procedure described in Example 3, stage E, but replacing 3-[(dimethylamino)methyl]-4-oxo-6-methoxy-9-methyl-2,3,4,9-tetrahydrothiopyrano[2,3-b]indole (hydrochloride) by 3-[(dimethylamino)methyl]-4-oxo-5-methoxy-9-methyl-2,3,4,9-tetrahydrothiopyrano[2,3-b]indole (hydrochloride), the expected product is obtained, salification being performed here with an alcoholic solution of maleic acid instead of an ethereal solution of hydrochloric acid.
Yield: 41%.
Melting point: 168°–170° C. Analysis: Calculation: C: 57.76, H: 5.07, N: 9.18, S: 7.01. Found: C: 58.18, H: 5.02, N: 8.94, S: 7.08.

EXAMPLE 5
3-[(2-Methyl-1-Imidazolyl)Methyl]-4-Oxo-7-Methoxy-9-Methyl-2,3,4,9-Tetrahydrothiopyrano[2,3-b]Indole (Hydrochloride)

Stage A: 1-Methyl-6-Methoxy-2-Indolinethione

Using the procedure described in Example 3, stage A, but replacing 5-methoxy-1-methyl-2-indolinone by 6-methoxy-1-methyl-2-indolinone, the expected product is obtained.
Yield: 76%.
Melting point: 135°–136° C.
Analysis Calculated: C: 62.15, H: 5.74, N: 7.25, S: 16.59. Found: C: 61.99, H: 5.91, N: 7.55, S: 16.31.

Stage B:
3-(1-Methyl-6-Methoxy-2-Indolylthio)Propanoic Acid

Using the procedure described in Example 3, stage B, but replacing 1-methyl-5-methoxy-2-indolinethione by 1-methyl-6-methoxy-2-indolinethione obtained in the preceding stage, the expected product is obtained.
Yield: 72%.
Melting point: 120°–122° C.

Analysis Calculated: C: 58.85, H: 5.70, N: 5.28, S: 12.08. Found: C: 59.01, H: 5.78, N: 5.41, S: 12.06.

Stage C:
4-OXO-7-METHOXY-9-METHYL-2,3,4,9-TETRAHYDROTHIOPYRANO[2,3-b]INDOLE

Using the procedure described in Example 3, stage C, but replacing 3-(1-methyl-5-methoxy-2-indolylthio)-propanoic acid by 3-(1-methyl-6-methoxy-2-indolylthio)-propanoic acid obtained in the preceding stage, the expected product is obtained.
Yield: 62%.
Melting point: 204°–206° C.
Analysis: Calculated: C: 63.14, H: 5.30, N: 5.66, S: 12.96. Found: C: 63.17, H: 5.56, N: 5.53, S: 12.87.

Stage D:
3-[(DIMETHYLAMINO)METHYL]-4-OXO-7-METHOXY-9-METHYL-2,3,4,9-TETRAHYDROTHIOPYRANO[2,3-b]INDOLE (HYDROCHLORIDE)

Using the procedure described in Example 3, stage D, but. replacing 4-oxo-6-methoxy-9-methyl-2,3,4,9-tetrahydrothiopyrano[2,3-b]indole by 4-oxo-7-methoxy-9-methyl-2,3,4,9-tetrahydrothiopyrano[2,3-b]indole obtained in the preceding stage, the expected product is obtained.
Yield: 48%. Melting point: 211°–212° C.
Analysis: Calculated: C: 56.38, H: 6.21, N: 8.22, S: 9.41, Cl: 10.40. C: 56.71, H: 5.85, N: 7.80, S: 9.75, Cl: 10.39.

Stage E:
3-[(2-METHYL-1-IMIDAZOLYL)METHYL]4-OXO-7-METHOXY-9-METHYL-2,3,4,9-TETRAHYDROTHIOPYRANO[2,3-b]INDOLE (HYDROCHLORIDE)

Using the procedure described in Example 3, stage E, but replacing 3-[(dimethylamino)methyl]-4-oxo-6-methoxy-]-methyl-2,3,4,9-tetrahydrothiopyrano[2,3-b]-indole (hydrochloride) by 3-[(dimethylamino)methyl]4-oxo-7-methoxy-9-methyl-2,3,4,9-tetrahydrythiopyrano[2,3-b]indole (hydrochloride), the expected product is obtained.
Yield: 32%.
Melting point: 154°–156° C.
Elemental analysis: Calculated: C: 57.21, H: 5.33, N: 11.12, S: 8.48, Cl: 9.38. Found: C: 56.67, H: 5.32, N: 11.03, S: 8.53, Cl: 9.42.

EXAMPLE 6
3-[(2-Methyl-1-Imidazolyl)Methyl]-4-Oxo-8-Methoxy-9-Methyl-2,3,4,9-Tetrahydrothiopyrano[2,3-B]Indole (Maleate)

Stage A: 1-Methyl-7-Methoxy-2-Indolinethione

Using the procedure described in Example 3, stage A, but replacing 5-methoxy-1-methyl-2-indolinone by 7-methoxy-1-methyl-2-indolinone, the expected product is obtained.
Yield: 78%.
Melting point: 114°–116° C.
Analysis: Calculated: C: 62.15, H: 5.74, N: 7.25, S: 16.59. Found: C: 62.00, H: 5.78, N: 7.13, S: 16.32.

Stage B: 3-(1-Methyl-7-Methoxy-2-Indolylthio) Propanoic Acid

Using the procedure described in Example 3, stage B, but replacing 1-methyl-5-methoxy-2-indolinethione by 1-methyl-7-methoxy-2-indolinethione obtained in the preceding stage, the expected product is obtained.

Yield: 75%.
Melting point: 120°-122° C.
Analysis: Calculated: C: 58.85, H: 5.70, N: 5.28, S: 12.08. Found: C: 59.02, H: 5.54, N: 5.28, S: 11.96.

Stage C: 4-Oxo-8-Methoxy-9-Methyl-2,3,4,9-Tetrahydrothiopyrano[2,3-b]Indole

Using the procedure described in Example 3, stage C, but replacing 3-(1-methyl-5-methoxy-2-indolylthio)-propanoic acid by 3-(1-methyl-7-methoxy-2-indolylthio)propanoic acid obtained in the preceding stage, the expected product is obtained.

Yield: 71%.
Melting point: 106°-108° C.
Analysis: Calculated: C: 63.14, H: 5.30, N: 5.66, S: 12.96. Found: C: 62.93, H: 5.37, N: 5.60, S: 12.97.

Stage D: 3-[(Dimethylamino)Methyl]-4-Oxo-8-Methoxy-9-Methyl-2,3,4,9-Tetrahydrothiopyrano[2,3-b]Indole (Hydrochloride)

Using the procedure described in Example 3, stage D, but replacing 4-oxo-6-methoxy-9-methyl-2,3,4,9-tetrahydrothiopyrano[2,3-b]indole by 4-oxo-8-methoxy-9-methyl-2,3,4,9-tetrahydrothiopyrano[2,3-b]indole, the expected product is obtained.

Yield: 53%.
Melting point: 190°-192° C.

Stage E: 3[(2-Methyl-1-Imidazolyl)Methyl]-4-Oxo-8-Methoxy-9-Methyl-2,3,4,9-Tetrahydrothipyrano[2,3-b]Indole (Maleate)

Using the procedure described in Example 4, stage E, but replacing 3-[(dimethylamino)methyl]-4-oxo-5-methoxy-9-methyl-2,3,4,9-tetrahydrothiopyrano[2,3-b]indole (hydrochloride) by 3-[(dimethylamino)methyl]-4-oxo-8-methoxy-9-methyl-2,3,4,9-tetrahydrothiopyrano[2,3-b]indole (hydrochloride), the expected product is obtained.

Yield: 36%.
Melting point: 178°-180° C.
Analysis: Calculated: C: 57.76, H: 5.07, N: 9.18, S: 7.01. Found: C: 57.65, H: 5.01, N: 8.72, S: 6.99.

EXAMPLE 7

3-[(2-Methyl-1-Imidazolyl)Methyl]-4-Oxo-6-Chloro-9-Methyl-2,3,4,9-Tetrahydrothiopyrano[2,3-b]Indole (Hydrochloride)

Using the procedure described in Example 1, but replacing 1-methyl-2-indolinone in stage A, by 1-methyl-5-chloro-2-indolinone, the product of the title is obtained.

Yield: 42%.
Melting point: 252°-254° C.
Analysis: Calculated: C: 53.41, H: 4.61, N: 10.99, S: 8.39, Cl: 18.55. Found: C: 52.76, H: 4.36, N: 11.31, S: 8.44, Cl: 18.59.

EXAMPLE 8

3-[(2-Methyl-1-Imidazolyl)Methyl]-4-Oxo-7-Fluoro-9-Methyl-2,3,4,9-Tetrahydrothiopyrano[2,3-b]Indole (Hydrochloride)

Using the procedure described in Example 1, but replacing 1-methyl-2-indolinone in stage A by 1-methyl-6-fluoro-2-indolinone, the product of the title is obtained.

EXAMPLE 9

3-[(2-Methyl-1-Imidazolyl)Methyl]-4-Oxo-8-Trifluoromethyl-9-Methyl-2,3,4,9-Tetrahydrothiopyrano[2,3-b]Indole (Hydrochloride)

Using the procedure described in Example 1, but replacing 1-methyl-2-indolinone in stage A by 1-methyl-7-trifluoromethyl-2-indolinone, the product of the title is obtained.

EXAMPLE 10

3-(1-Pyrrolidinylmethyl)4-Oxo-9-Methyl-2,3,4,9-Tetrahydrothiopyrano[2,3-b]Indole (Hydrochloride)

A mixture of 2.50 g (0.008 mol) of 3-[(dimethylamino)methyl]-4-oxo-9-methyl-2,3,4,9-tetrahydrothiopyrano[2,3-b]indole hydrochloride obtained in Example 1, stage E and 1.78 g (0.025 mol) of pyrrolidine in 40 ml of water is heated to reflux for 10 hours. After the mixture is cooled, the precipitate formed is drained, washed with water, dried and dissolved in 40 ml of tetrahydrofuran and the solution is treated with an ethereal solution of hydrochloric acid. The precipitate formed is drained, washed with ether and recrystallized in ethanol.

Yield: 61%.
Melting point: 222°-224° C.
Analysis: Calculated: C: 60.61, H: 6.28, N: 8.32, S: 9.52, Cl: 10.52. Found: C: 60.74, H: 6.47, N: 8.27, S: 9.57, Cl: 10.53.

EXAMPLE 11

3-[(2-Methyl-1-Imidazolyl)Methyl]-3,9-Dimethyl-4-Oxo-2,3,4,9-Tetrahydrothiopyrano[2,3-b]Indole (Hydrochloride)

Stages A to E: 3,9-Dimethyl-3-[(Dimethylamino)Methyl]-4-Oxo-2,3,4,9-Tetrahydrothiopyrano[2,3-b]Indole (Hydrochloride)

Using the procedure described in Example 1, but replacing acrylic acid in stage B by methacrylic acid, the expected product is obtained.

Yield: 78%.
Melting point: 220°-222° C.
Analysis: Calculated: C: 59.15, H: 6.52, N: 8.62, S: 9.87, Cl: 10.91. Found: C: 59.51, H: 6.59, N: 8.36, S: 9.71, Cl: 10.92.

Stage F: 3-[(2-Methyl-1-Imidazolyl)Methyl]-3,9-Dimethyl-4-Oxo-2,3,4,9-Tetrahydrothiopyrano[2,3-b]Indole (Hydrochloride)

Using the procedure described in stage F of Example 1, but replacing 3-[(dimethylamino)methyl]-4-oxo-9-methyl-2,3,4,9-tetrahydrothiopyrano[2,3-b]indole hydrochloride by 3,9-dimethyl-3-[(dimethylamino)methyl]-4-oxo-2,3,4,9-tetrahydrothiopyrano[2,3-b]indole hydrochloride obtained in the preceding stage, the expected product is obtained.

EXAMPLE 12

3-(3,5-Dimethyl-1-Piperazinylmethyl)-4-Oxo-9-Methyl-2,3,4,9-Tetrahydrothiopyrano[2,3-b]Indole (Dihydrochloride)

By replacing pyrrolidine in Example 10 by 2,6-dimethylpiperazine, the product of the title is obtained.
Yield: 71%.
Melting point: 202°–204° C.
Analysis: Calculated: C: 54.80, H: 6.54, N: 10.09, S: 7.70, Cl: 17.03. Found C: 54.74, H: 6.34, N: 9.92, S: 8.05, Cl: 17.18.

EXAMPLE 13

3-Piperidinomethyl-4-Oxo-9-Methyl-2,3,4,9-Tetrahydrothiopyrano[2,3-b]Indole (Hydrochloride)

By replacing pyrrolidine in Example 10 by piperidine, the product of the title is obtained.
Yield: 58%.
Melting point: 211°–213° C.
Analysis: Calculated: C: 61.61, H: 6.61, N: 7.98, S: 9.14, Cl: 10.10. Found: C: 61.51, H: 7.02, N: 7.97, S: 9.20, Cl: 10.21.

EXAMPLE 14

3-Morpholinomethyl-4-Oxo-9-Methyl-2,3,4,9-Tetrahydrothiopyrano[2,3-b]Indole (Hydrochloride)

By replacing pyrrolidine in example 10 by morpholine, the expected product is obtained.

EXAMPLE 15

3-[4-(2-Methoxyphenyl)-1-Piperazinylmethyl]-4-Oxo-9-Methyl-2,3,4,9-Tetrahydrothiopyrano[2,3-b]Indole (Hydrochloride)

By replacing pyrrolidine in Example 10 by 1-(2-methoxyphenyl)piperazine, the expected product is obtained.

EXAMPLES 16 TO 18

By replacing 3-[(dimethylamino)methyl]-4-oxo-9-methyl-2,3,4,9-tetrahydrothiopyrano(2,3-b)indole hydrochloride in Examples 10, 12 and 13 by 3-[(dimethylamino)methyl]-4-oxo-5-methoxy-9-methyl-4-oxo-2,3,4,9-tetrahydrothiopyrano[2,3-b]indole hydrochloride, obtained in Example 4, stage D, the following are obtained:

Example 16: 3-(1-PYRROLIDINYLMETHYL)-4-OXO-5-METHOXY-9-METHYL-2,3,4,9-TETRAHYDROTHIOPYRANO[2,3-b]INDOLE (HYDROCHLORIDE)
Example 17: 3-(3,5-DIMETHYL-1-PIPERAZINYLMETHYL)4-OXO-5METHOXY-9-METHYL-2,3,4,9-TETRAHYDROTHIOPYRANO[2,3-b]INDOLE (HYDROCHLORIDE)
Example 18: 3-PIPERIDINOMETHYL-4-OXO-5-METHOXY-9-METHYL-2,3,4,9-TETRAHYDROTHIOPYRANO[2,3-b]INDOLE (HYDROCHLORIDE)
Example 19: 3-[(2-METHYL-1-IMIADAZOLYL)-METHYL]-4-OXO-9-METHYL-2,3,4,9-TETRAHYDROTHIOPYRANO[2,3-b]INDOLE S-OXIDE (HYDROCHLORIDE)

A solution of 1.38 g (0.008 mol) of meta-chloroperbenzoic acid in 20 ml of chloroform is added slowly to a solution, cooled to 0° C., of 1.56 g (0.005 mol) of 3-[(2-methyl-1-imidazolyl)methyl]-4-oxo-9-methyl-2,3,4,9-tetrahydrothiopyrano[2,3-b]indole (obtained in Example 1) in 50 ml of chloroform. The mixture is stirred at 5° C. for 1 hour and then at room temperature for 1 hour. After filtration, the organic phase is washed with 5% strength sodium hydroxide and then with water, dried and evaporated. The product is purified by chromatography on silica, eluting with a methylene chloride/methanol mixture (95:5). The product obtained is dissolved in 80 ml of tetrahydrofuran and the solution is treated with 2 ml of an ethereal solution of hydrochloric acid. The precipitate is drained, washed with ether, dried and recrystallized in ethanol.
Yield: 30%.
Melting point: 175°–178° C.
Analysis: Calculated: C: 56.12, H: 4.99, N: 11.55, S: 8.81, Cl: 9.74. Found: C: 56.23, H: 5.21, N: 11.46, S: 8.77, Cl: 9.86.

EXAMPLE 20

4-[(2-Methyl-1-Imidazolyl)Methyl]-5-Oxo-10-Methyl-2,3,4,5,10-Pentahydrothiepino[2,3-b]Indole STAGE A: Ethyl 4-(1-Methyl-2-Indolylthio)Butanoate A suspension composed of 11.43 g (0.07 mol) of 1-methyl-2-indolinethione, obtained in Example 1, stage A, and 13.70 g (0.07 mol) of ethyl 4-bromobutanoate in 30 ml of acetone is stirred at 20° C. for 5 hours in the presence of 11.75 g (0.096 mol) of finely ground potassium carbonate. The mixture is filtered, the solvent is evaporated off and the oil obtained is used directly in the next stage.

STAGE B: 4-(1-Methyl-2-Indolylthio)Butanoic Acid 70 ml of normal sodium hydroxide are added to a solution of 18.30 g of ethyl 4-(1-methyl-2-indolylthio)butanoate, obtained in the preceding stage, in 250 ml of ethanol. After 1 hour of heating under reflux, the reaction medium is evaporated and the residue is taken up with water. The aqueous phase is washed with ethyl acetate and acidified with aqueous hydrochloric acid solution. The precipitate is drained, washed with water, dried and recrystallized in ethanol.
Yield: 80%.
Melting point: 133°–135° C.
Analysis: Calculated: C: 62.62, H: 6.06, N: 5.62, S: 12.86. Found: C: 61.95, H: 6.10, N: 5.31, S: 12.57.

STAGE C:
5-Oxo-10-Methyl-2,3,4,5,10-Pentahydrothiepino[2,3-b]Indole

A mixture of 15 g (0.060 mol) of 4-(1-methyl-2-indolylthio)butanoic acid, obtained in the preceding stage, and 80 g of polyphosphate ester in 600 ml of chloroform is stirred at room temperature for 16 hours and under a nitrogen atmosphere. After dilution with 1.3 l of ice-cold water, the organic phase is separated after settling has occurred and the aqueous phase is extracted with chloroform. The organic phases are combined, washed with 10% strength aqueous sodium bicarbonate solution and then with water, dried and concentrated under vacuum. The residue is recrystalized in acetonitrile.
Yield: 92%.
Melting point: 165°–166° C.

Analysis: Calculated: C: 67.50, H: 5.66, N: 6.06, S: 13.86. Found: C: 68.23, H: 5.89, N: 6.52, S: 13.82.

Stage D:
4-[(Dimethylamino)Methyl]-5-Oxo-10-Methyl-2,3,4,5,10-Pentahydrothiepino[2,3-b]Indole (Hydrochloride)

A suspension of 12.6 g (0.055 mol) of 5-oxo-10-methyl-2,3,4,5,10-pentahydrothiepino[2,3-b]indole, 9.10 g (0.11 mol) of dimethylamine hydrochloride and 3.50 g of paraformaldehyde in 200 ml of acetic acid is stirred at 100° C. for 2 hours 30 minutes under a nitrogen atmosphere. The mixture is cooled, the solvent is evaporated off and the residue is dissolved in a water/acetic acid mixture (80:20). The aqueous phase is washed with ethyl acetate and alkalinized with concentrated ammonia solution. The oily precipitate is extracted with methylene chloride and the organic phase is washed with saturated aqueous sodium chloride solution and evaporated. The residue is dissolved in 80 ml of tetrahydrofuran and the solution is treated with 15 ml of an ethereal solution of hydrochloric acid at 0° C. for 3 hours. The precipitate is drained, washed with ethyl ether, dried and recrystallized in an ethanol/ether mixture.
Yield: 54%.
Melting point: 232°–233° C.
Analysis: Calculated: C: 59.15, H: 6.52, N: 8.62, S: 9.87, Cl: 10.91. Found: C: 58.83, H: 6.44, N: 8.32, S: 9.69, Cl: 10.70.

Stage E:
4-[(2-Methyl-1-Imidazolyl)Methyl]-5-Oxo-10-Methyl-2,3,4,5,10-Pentahydrothiepino[2,3-b]Indole (Hydrochloride)

A solution of 2.46 g (0.03 mol) of 2-methylimidazole and 3.25 g (0.01 mol) of 4-[(dimethylamino)methyl]-5-oxo-10-methyl-2,3,4,5,10-pentahydrothiepino[2,3-b]indole hydrochloride in 40 ml of water is heated to 100° C. for 20 hours. After the mixture is cooled, the solid residue is drained, washed with water and dried under vacuum. The residue obtained is dissolved in 80 ml of hot ethanol and treated with 4 ml of an ethereal solution of hydrochloric acid for 30 minutes at 40° C. The solvent is evaporated off and the residue is crystallized in ethanol.
Yield: 75%.
Melting point: 222°–224° C.
Analysis:
Calculated: C: 59.74, H: 5.57, N: 11.61, S: 8.86, Cl: 9.80. Found: C: 59.67, H: 5.65, N: 11.37, S: 8.99, Cl: 9.64.

EXAMPLE 21

3-[(2-Methyl-1-Imidazolyl)Methyl]-4-Oxo-9-Methylsulfonyl-2,3,4,9-Tetrahydrothiopyrano[2,3-b]Indole (Hydrochloride)

Stage A: 3-(2-Indolylthio)Propionic Acid

One liter of triethylamine is added slowly in the course of 2 hours 30 minutes to a vigorously stirred suspension of 194 g (1.3 mol) of 2-indolinethione (prepared according to Y. Nakisumi and Coll. Chem. Pharm. Bull. 1984, 32, (3), 877) in 108 g (1.5 mol) of acrylic acid. The mixture is brought to reflux for 12 hours while stirring is maintained, and then cooled and concentrated under vacuum. The residue is taken up with 10% strength aqueous sodium bicarbonate solution and the mixture is filtered. The filtrate is acidified with aqueous hydrochloric acid solution. The precipitate formed is drained, washed with water and dried. It is recrystallized in toluene.
Yield: 75%.
Melting point: 116°–118° C.
Analysis: Calculated: C: 59.71, H: 5.01, N: 6.33, S: 14.49. Found: C: 59.72, H: 4.89, N: 6.19, S: 14.16.

Stage B:
4-Oxo-2,3,4,9-Tetrahydrothiopyrano[2,3-b]Indole

A mixture of 88.5 g (0.4 mol) of 3-(2-indolylthio)propionic acid and 300 g of polyphosphate ester in 3.5 liters of chloroform is stirred for 16 hours at room temperature and under a nitrogen atmosphere. The mixture is diluted with 3 liters of ice-cold water, the organic phase is separated after settling has occurred and the aqueous phase is extracted with chloroform. The organic phases are combined, washed with 10% strength aqueous sodium bicarbonate solution and then with water, dried and concentrated on a water bath under vacuum. The residue is recrystallized in ethanol, the crystals obtained are removed and the filtrate is concentrated.
Yield: 35%.
Melting point: 226°–228° C.
Analysis: Calculated: C: 65.00, H: 4.46, N: 6.89, S: 15.77. C: 64.71, H: 4.60, N: 6.84, S: 15.74.

Stage C:
3-[(Dimethylamino)Methyl]-4-Oxo-2,3,4,9-Tetrahydrothiopyrano[2,3-b]Indole (Hydrochloride)

A mixture of 4.10 g (0.2 mol) of 4-oxo-2,3,4,9-tetrahydrothiopyrano[2,3-b]indole, 3.26 g (0.04 mol) of dimethylamine hydrochloride and 1 g of paraformaldehyde in 50 ml of acetic acid is stirred vigorously at 100° C. under a nitrogen atmosphere and for 45 minutes. After the mixture is cooled, the solvent is evaporated off, the residue is dissolved in 80 ml of water and the aqueous phase is washed with ethyl acetate and alkalinized with concentrated ammonia solution. The precipitate is extracted with methylene chloride and the solution is washed with water saturated with sodium chloride and then concentrated. The residue is dissolved in 50 ml of hot ethanol and the solution is treated at 40° C. with 7 ml of an ethanolic solution of hydrochloric acid. After dilution with ethyl ether, the precipitate is drained, washed with ethyl ether, dried and recrystallized in ethanol.
Yield: 76%.
Melting point: 235°–237° C.
Analysis: Calculated: C: 56.65, H: 5.77, N: 9.44, S: 10.80, Cl: 11.94, Found: C: 56.76, H: 6.02, N: 9.43, S: 10.55, Cl: 11.64.

Stage D:
3-[(2-Methyl-1-Imidazolyl)Methyl]-4-Oxo-2,3,4,9-Tetrahydrothiopyrano[2,3-b]Indole 5.60 ml (0.09 mol) of iodomethane are added to a solution of 23.43 g (0.09 mol) of 3-[(dimethylamino)methyl]-4-oxo-2,3,4,9-tetrahydrothiopyrano[2,3-b]indole (hydrochloride) in 250 ml of dimethylformamide. The mixture is stirred at room temperature for 1 hour, a solution of 22.17 g (0.27 mol) of 2-methylimidazole in 50 ml of dimethylformamide is then added and the reaction medium is thereafter heated to 100° C. for 36 hours. After the mixture is cooled, 500 ml of 2N aqueous sodium carbonate solution are added and the resulting mixture is extracted three times with ethyl acetate. The organic phases are combined, washed with water (200 ml), dried and concentrated under vacuum. The product is chromatographed on silica, eluting with a methylene chloride/ethanol/ammonia solution mixture (92:8:0.5). The residue is recrystallized in acetonitrile.
Yield: 45%.
Melting point: 231°–233° C.

Stage E:
3-[(2-Methyl-1-Imidazolyl)Methyl]-4-Oxo-2,3,4,9-Tetrahydrothiopyrano[2,3-b]Indole (Hydrochloride)

1 g of the product obtained in the preceding stage is dissolved in 20 ml of ethanol at 50° C. and the solution is treated with 2 ml of an ethanolic solution of hydrochloric acid (5.2 N) for 30 minutes. The solvent is evaporated off and the residue is recrystallized in ethanol.
Melting point: 228°–230° C.
Analysis: Calculated: C: 57.57, H: 4.83, N: 12.59, S: 9.60Cl: 10.62. Found: C: 57.49, H: 5.25, N: 12.10, S: 9.47, Cl: 10.44.

Stage F:
3-[(2-Methyl-1-Imidazolyl)Methyl]-4-Oxo-9-Methysulfonyl-2,3,4,9-Tetrahydrothiopyrano[2,3-b]Indole (Hydrochloride)

0.20 g (0.0042 mol) of sodium hydride, at a concentration of 50% in oil, is added in the course of 30 minutes and under a nitrogen atmosphere to a solution of 1.19 g (0.004 mol) of 3-[(2-methyl-1-imidazolyl)methyl]-4-oxo-2,3,4,9-tetrahydrothiopyrano[2,3-b]indole in 20 ml of dimethylformamide, and 0.325 ml (0.0042 mol) of methanesulfonyl chloride is then added. The mixture is stirred for 4 hours at room temperature, 150 ml of 2N sodium carbonate solution are added and the resulting mixture is extracted three times with ethyl acetate. The organic phases are combined, dried and evaporated. The residue (1.35 g) is chromatographed on silica gel, eluting with a methylene chloride/ethanol mixture (92:8). The residue obtained is dissolved in 20 ml of ethanol and the solution is treated with 3 ml of an ethereal solution of hydrochloric acid at 10° C. for 1 hour. The precipitate is drained, washed with ethyl ether and recrystallized in acetonitrile.
Yield: 30%.
Melting point: 228°–230° C.
Analysis: Calculated: C: 49.57, H: 4.40, N: 10.20, S: 15.57, Cl: 8.61. Found: C: 50.48, H: 4.76, N: 10.50, S: 15.26, Cl: 8.55.

EXAMPLE 22

3-[(2-Methyl-1-Imidazolyl)Methyl]-4-Oxo-9-(para-Toluenesulfonyl)-2,3,4,9-Tetrahydrothiopyrano[2,3-b]Indole (Hydrochloride)

Using the procedure described in Example 21, but replacing methanesulfonyl chloride in stage F by paratoluenesulfonyl chloride, the expected product is obtained.

EXAMPLE 23

3-(1,1,2-Trimethylguanidinomethyl)-4Oxo-9-Methyl-2,3,4,9-Tetrahydrothiopyrano[2,3-b]Indole Hydrochloride Stage A
3-[(10,11-Dihydro-5H-Dibenzo[a,d]Cyclohepten-5-YL)Aminomethyl]-4-Oxo-9-Methyl-2,3,4,9-Tetrahydrothiopyrano[2,3-b]Indole Hydrochloride A mixture of 22 g of 3-[(dimethylamino)methyl]-4-oxo-9methyl-2,3,4,9-tetrahydrothiopyrano[2,3-b]indole hydrochloride, obtained in Example 1, stage E, and 29.62 g (0.14 mol) of 10,11-dihydro-5H-dibenzo[a,d]cyclohepten-5-ylamine in 300 ml of water is stirred vigorously at a temperature in the region of 90° C. under a nitrogen atmosphere for 20 hours. After the mixture is cooled, the residue obtained is drained and dried and chromatographed under silica, eluting with a methylene chloride/methanol mixture (97:3). The solid obtained is dissolved in 150 ml of ethanol and treated with an ethereal hydrochloric acid solution. The precipitate formed is drained, washed with ethyl ether and recrystallized in ethanol.
Yield: 82%.
Melting point: 217°–218° C.
Analysis: Calculated: C: 70.79, H: 5.73, N: 5.90, S: 6.75, Cl: 7.46. Found: C: 70.73, H: 5.51, N: 6.00, S: 6.81, Cl: 7.45.

Stage B:
3-Aminomethyl-4-Oxo-9-Methyl-2,3,4,9-Tetrahydrothiopyrano [2,3-b]Indole Hydrochloride A solution of 27.10 g (0.057 mol) of 3-[(10,11-dihydro-5H-dibenzo[a,d]cyclohepten-5yl)aminomethyl]-4-oxo-2,3,4,9-tetrahydrothiopyrano[2,3-b]indole hydrochloride obtained in the preceding stage, in 600 ml of 60% strength aqueous acetic acid is heated to reflux for 6 hours. After the mixture is cooled and filtered, the filtrate is evaporated under vacuum, the residue is taken up in 200 ml of ethanol and the solution is treated with 30 ml of an ethereal solution of hydrochloric acid. After dilution with ether, the product is drained, washed with ether and recrystallized in methanol.
Yield: 91%.
Melting point: 255°–257° C.
Analysis: Calculated: C: 55.22, H: 5.35, N: 9.91, S: 11.34, Cl: 12.54. Found: C: 55.45, H: 5.41, N: 9.94, S:11.48, Cl:12.47.

Stage C: 3-(1,1,2-Trimethylguanidinomethyl)-4-Oxo-9-Methyl-2,3,4,9-Tetrahydrothiopyrano[2,3-b]Indole Hydrochloride The 3-aminomethyl-4-oxo-9-methyl-2,3,4,9-tetrahydrothiopyrano[2,3-b]indole hydrochloride obtained in the preceding stage is dissolved in water, the solution is neutralized with potassium bicarbonate and extracted with methylene chloride and the organic phase is dried and evaporated. 4.90 g (0.02 mol) of the product thereby obtained are dissolved in 80 ml of pyridine. 5.20 g (0.02 mol) of N,N,N',S-tetramethylisothiouronium hydriodide are added and then this solution is heated to 90° C. for 2 hours 30 minutes. The solvent is evaporated off and the oily residue is chromatographed on silica, eluting with a chloroform/methanol mixture (92:8). The product obtained is dissolved in a mixture of 70 ml of ethanol and 20 ml of water, and treated with 3 g of silver carbonate with brisk stirring for 1 hour. The mixture is filtered through celite, the filtrate is evaporated and the residue is taken up in 30 ml of ethanol and treated with an ethereal solution of hydrochloric acid. After dilution with ether, the precipitate is drained, washed with ether and recrystallized in acetonitrile.
Yield: 42%.
Melting point: 204°–206° C.
Analysis: Calculated: C: 55.65, H: 6.32, N: 15.27, S: 8.74, Cl: 9.66. Found: C: 55.80, H: 6.44, N: 15.20, S: 8.82, Cl: 9.58.

EXAMPLE 24:

3-[(4,5-Dihydro-2-Imidazolyl)Aminomethyl]-4-Oxo-9-Methyl-2,3,4,9-Tetrahydrothiopyrano[2,3-b]Indole Hdyrochloride Using the procedure described in Example 23, but replacing N,N,N',S-tetramethylisothiouronium hydriodide in stage C by 2-methylmercapto-4,5-dihydroimidazole hydriodide, the expected product is obtained.

Yield: 66%.

Melting point: 245°–247° C.

Analysis: Calculated: C: 54.77, H: 5.46, N: 15.97, S: 9.14, Cl: 10.10. Found: C: 54.46, H: 5.55, N: 15.93, S: 9.17, Cl: 9.99.

EXAMPLE 25:

3-[(2-Methyl-1-Imidazolyl)Methyl]-2-Phenyl-4-Oxo-9-Methyl-2,3,4,9-Tetrahydrothiopyrano[2,3-b]Indole (Hydrochloride)

Using the procedure described in Example 1, but replacing acrylic acid in stage B by cinnamic acid, the product of the title is obtained.

Yield: 65%.

Melting point: 195°–197° C.

Analysis: Calculated: C: 65.16, H: 5.23, N: 9.91, S: 7.56, Cl: 8.36. Found: C: 64.80, H: 5.45, N: 9.65, S: 7.45, Cl: 8.39.

EXAMPLE 26

3-[(2-Methyl-1-Imidazolyl)Methyl]-2-(4-Methylphenyl)-4-Oxo-9-Methyl-2,3,4,9-Tetrahydrothiopyrano[2,3-b]Indole (Hydrochloride)

Using the procedure described in Example 1, but replacing acrylic acid in stage B by 4-methylcinnamic acid, the product of the title is obtained.

EXAMPLE 27

3-[(2-Phenyl-1-Imidazolyl)Methyl]-4-Oxo-9-Methyl-2,3,4,9-Tetrahydrothiopyrano[2,3-b]Indole (Hydrochloride)

Using the procedure described in Example 1, but replacing 2-methylimidazole in stage F by 2-phenylimidazole, the product of the title is obtained.

EXAMPLE 28

3-(1-Benzimidazolylmethyl)-4-Oxo-9-Methyl-2,3,4,9-Tetrahydrothiopyrano[2,3-b]Indole (Hydrochloride)

Using the procedure described in Example 1, but replacing 2-methylimidazole in stage F by benzimidazole, the product of the title is obtained.

EXAMPLE 29

3-(Thiomorpholinomethyl)-4-Oxo-9-Methyl-2,3,4,9-Tetrahydrothiopyrano[2,3-b]Indole (Hydrochloride)

Using the procedure described in Example 14, but replacing morpholine by thiomorpholine, the product of the title is obtained.

EXAMPLE 30

Pharmacological Study Of The Compounds Of The Invention: Inhibition Of The Bezold-Jarisch Effect This study is carried out on Charles River rats weighing between 350 and 400 g, anesthetized with a dose of 1.25 g.kg$^{-1}$ of urethane administered intraperitoneally. The arterial blood pressure is recorded on a carotid artery by means of a Statham P 23 dB pressure cell. The heart rate is recorded from the arterial blood pressure using a cardiotachometer. The recordings are carried out on a GOULD 2400 recorder. A catheter is placed in the jugular vein and reaches the animals right atrium. The Bezold-Jarisch effect is induced by a rapid injection of serotonin at a dose of 40 μg/kg intravenously into the right atrium. Cardiac slowing is associated with a drop in arterial blood pressure originating from stimulation of the afferent vagal fibres chiefly localized in the right ventricle.

The test products are administered intravenously at doses of 10 μg/kg or 50 μg/kg. A Bezold-Jarisch effect is induced at one or more of the following times: 5, 15, 30, 45 and 60 minutes after injection of the test products.

The percentage inhibition of the reflex bradycardia is evaluated from the heart rate trace.

The compounds of the invention showed a potent inhibitory effect on the Bezold-Jarisch effect.

Thus, when administered at a dose of 50 μg/kg, the compounds of Examples 1 and 20 cause a 95% antagonism five minutes after their administration, the effect of which antagonism persists over a period of time. In effect, this antagonism remains in the region of 95% fifteen minutes after the administration of 50 μg/kg of either of these two compounds. One hour after administration of 50 μg/kg of the compound of Example 20, an antagonism of the order of 60% is still observed.

By way of comparison, the reference compound GR 38032, administered at an identical dose, causes a 90% antagonism five minutes after its administration. This level has become only 55% 15 minutes after administration, and falls to 25% one hour after administration.

These results show the obvious superiority of the compounds of the invention.

EXAMPLE 31

Pharmaceutical Composition

Tablet containing 2.5 mg of 3-[(2-methyl-1-imidazolyl)methyl]-4-oxo-9-methyl-2,3,4,9-tetrahydrothiopyrano[2,3-b]indole (hydrochloride).

Preparation formula for 1000 tablets:

| | |
|---|---|
| 3-[(2-Methyl-1-imidazolyl)-methyl]-4-oxo-9-methyl-2,3,4,9-tetrahydrothiopyrano[2,3-b]indole (hydrochloride) | 2.5 g |
| Hydroxypropylcellulose | 1.5 g |
| Wheat starch | 12 g |
| Lactose | 120 g |
| Magnesium stearate | 2 g |
| Talc | 2 g |

We claim:

1. A compound of formula (I):

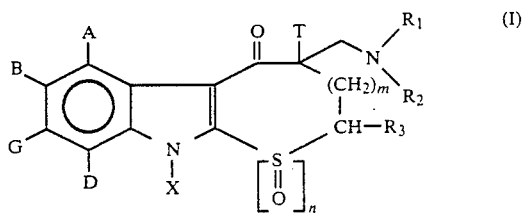

in which:

A, B, G and D, which may be identical or different, each is a hydrogen atom or a halogen atom, a lower alkoxy group or alternatively a linear or branched lower alkyl group unsubstituted or substituted with one or more halogen atoms, X is a hydrogen atom, a linear or branched lower alkyl group or a group SO₂E in which E is a linear or branched lower alkyl group or phenyl unsubstituted or substituted with a linear or branched lower alkyl group, T is a hydrogen atom or a lower alkyl group, $R_3$ is a hydrogen atom or a linear or branched lower alkyl group or an aryl group unsubstituted or substituted with one or more linear or branched lower alkyl groups, n and m, which may be identical or different, each is 0 or 1, $R_1$ and $R_2$, which may be identical or different, each is a hydrogen atom or a linear or branched lower alkyl group, or alternatively, $R_1$ and $R_2$, together with the nitrogen atom to which they are attached, form a heterocyclic system selected from the group consisting of imidazolyl, pyrrolidinyl, piperidinyl, piperazinyl, morpholinyl, benzimidazolyl, and thiomorpholinyl, said system being unsubstituted or substituted with one or more linear or branched lower alkyl or alkoxy groups or with phenyl which is itself unsubstituted or substituted with one or more lower alkyl, lower alkoxy or trifluoromethyl groups or alternatively with one or more halogen atoms, or alternatively, $R_1$ is a group

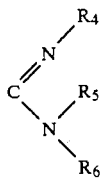

in which $R_4$, $R_5$ and $R_6$, which may be identical or different, each is a hydrogen atom or a linear or branched lower alkyl group, or alternatively $R_4$ forms with $R_5$ a bridge (CH₂)p, p being 2 to 4, inclusive, or alternatively $R_1$ is a 10,11-dihydro-5H-dibenzo[a,d]cyclohepten-5-yl group and $R_2$ is a hydrogen atom, where appropriate, its isomers and also its addition salts with a pharmaceutically-acceptable acid, on the understanding that lower alkyl or lower alkoxy group means such a group comprising 1 to 6 carbon atoms, inclusive.

2. A compound as claimed in claim 1, for which n is 0, X denotes a linear or branched lower alkyl group and $R_1$ and $R_2$ form, together with the nitrogen ato to which they are attached, an imidazole ring unsubstituted or substituted with one or more linear or branched lower alkyl or alkoxy groups or with phenyl which is itself unsubstituted or substituted with a lower alkyl, lower alkoxy or trifluoromethyl group or alternatively a halogen atom, its isomers and also its addition salts with a pharmaceutically-acceptable acid.

3. A compound as claimed in one of claim 1, for which $R_1$ and $R_2$ form, together with the nitrogen atom to which they are attached, a 2-methylimidazole group.

4. A compound as claimed in one of claim 1, which is 3-[(2-methyl-1-imidazolyl)methyl]-4-oxo-9-methyl-2,3,4,9-tetrahydrothiopyrano[2,3-b]indole, and also its addition salts with a pharmaceuticallyacceptable acid.

5. A compound as claimed in one of claim 1, which is 4-[(2-methyl-1-imidazolyl)methyl]-5-oxo-10-methyl-2,3,4,5,10-pentahydrothiepino[2,3-b]indole, and also its addition salts with a pharmaceutically-acceptable acid.

6. A pharmaceutical composition containing, as active principle, an effective amount of at least one compound as claimed in one of claim 1, in combination with one or more pharmaceutically-acceptable, non-toxic, inert vehicles or excipients.

7. A method for treating an animal or human living body afflicted with a disease resulting from a dysfunction of the serotoninergic system and, in particular, painful episodes, anxiety, schizophrenia vomiting and, in particular, which follow the administration of anticancer treatments, heart rhythm disorders, gastrointestinal upsets and also cognitive disorders and especially dementia states and memory disorders, consisting essentially of the step of administering to the said living body an amount of a compound of claim 1 which is suitable for alleviation of said condition.

8. A compound as claimed in claim 2, for which $R_1$ and $R_2$ form, together with the nitrogen atom to which they are attached, a 2-methylimidazole group.

* * * * *

UNITED STATES PATENT AND TRADEMARK OFFICE
CERTIFICATE OF CORRECTION

PATENT NO. : 5,030,646

DATED : July 9, 1991

INVENTOR(S) : Charles Malen, Jean-Michel Lacoste and Michel Laubie

It is certified that error appears in the above-identified patent and that said Letters Patent is hereby corrected as shown below:

Title Page, [54], last word of title; "COMPOUND" should read -- COMPOUNDS --

Col. 5, lines 1-12, in the formula, the top right-hand corner; "(I/C1)" should be moved up or to the right-hand side;

Col. 6, lines 1-5, in the formula, the top right-hand corner; "(I/D)" should be moved up or to the right-hand side;

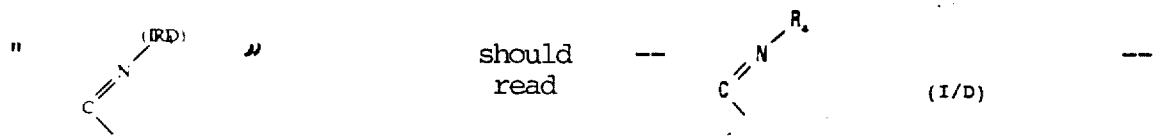

Col. 8, line 58; "[2,3-]" should read -- [2,3-b] --
Col. 8, line 58; "Indole" should be in regular print, not bold print
Col. 9, line 43; "$^1$ H" should read -- $^1$H --
Col. 9, line 52; "-Tetrahydrothipyrano[2,3-b]Indole" should read
-- -Tetrahydrothiopyrano[2,3-b]Indole --
Col. 11, line 48; "-indolythio)propanoic" should read
-- -indolylthio)propanoic --
Col. 14, line 20; "-TETRAHYDR-" should read -- -TETRAHYDRO- --
Col. 14, line 32; "10.40. C:" should read -- 10.40. Found: C: --

UNITED STATES PATENT AND TRADEMARK OFFICE
CERTIFICATE OF CORRECTION

PATENT NO.  : 5,030,646

DATED       : July 9, 1991

INVENTOR(S) : Charles Malen, Jean-Michel Lacoste and Michel Laubie

It is certified that error appears in the above-identified patent and that said Letters Patent is hereby corrected as shown below:

Col. 14, line 43; "methoxy-]-methyl-" should read -- methoxy-9-methyl- --
Col. 14, line 44; "3-[(dimethylamino)methyl]4-" should read
 -- 3-[(dimethylamino)methyl]-4- --
Col. 15, line 41; "-Tetrahydrothipyrano[2,3-" should read
 -- -Tetrahydrothiopyrano[2,3- --
Col. 17, line 14; "Found C:" should read -- Found: C: --
Col. 17, line 57; "METHYL)4-OXO-5METHOXY-" should read
 -- METHYL)-4-OXO-5-METHOXY- --
Col. 20, line 25; "15.77. C:" should read -- 15.77. Found: C: --
Col. 21, line 17; "9.60Cl:" should read -- 9.60, Cl: --
Col. 21, line 59; "-4Oxo-" should read -- -4-Oxo- --
Col. 21, line 67; "oxo-9methyl-" should read -- oxo-9-methyl- --
Col. 23, line 5; "Hdyrochloride" should read -- Hydrochloride --
Col. 26, line 11; "ato" should read -- atom --
Col. 26, lines 19, 22, 26, & 32; in all four (4) occurrences delete "one of"

Col. 26, line 25; "pharmaceuticallyacceptable" should read
 -- pharmaceutically-acceptable --

Signed and Sealed this

Fifth Day of January, 1993

Attest:

DOUGLAS B. COMER

Attesting Officer

Acting Commissioner of Patents and Trademarks